United States Patent
Cole

(10) Patent No.: US 6,203,680 B1
(45) Date of Patent: Mar. 20, 2001

(54) ELECTROPHORESIS GELS

(75) Inventor: Kenneth D. Cole, Gaithersburg, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 0 days.

(21) Appl. No.: 09/245,412

(22) Filed: Feb. 5, 1999

Related U.S. Application Data

(60) Provisional application No. 60/073,756, filed on Feb. 5, 1998.

(51) Int. Cl.⁷ .................. G01N 27/26; G01N 27/447
(52) U.S. Cl. .................. 204/469; 204/462; 204/613
(58) Field of Search .................. 204/469, 462, 204/613

(56) References Cited

U.S. PATENT DOCUMENTS

| | | | |
|---|---|---|---|
| 4,326,052 | 4/1982 | Kang et al. | 536/123 |
| 4,377,636 | 3/1983 | Kang et al. | 435/101 |
| 4,385,123 | 5/1983 | Kang et al. | 435/253.6 |
| 4,552,640 * | 11/1985 | Kartenbeck | 204/613 |
| 4,699,706 * | 10/1987 | Burd et al. | 204/613 |
| 5,143,646 | 9/1992 | Nochumson et al. | 204/469 |
| 5,219,599 * | 6/1993 | Cox et al. | 426/104 |
| 5,238,065 * | 8/1993 | Mondshine et al. | 166/300 |
| 5,277,915 | 1/1994 | Provonchee et al. | 424/485 |
| 5,334,640 * | 8/1994 | Desai et al. | 524/56 |
| 5,371,208 | 12/1994 | Kozulic | 204/403 X |
| 5,498,705 * | 3/1996 | Oin | 536/20 |
| 5,541,255 | 7/1996 | Kozulic | 525/54.3 |
| 5,550,189 * | 8/1996 | Qin et al. | 525/54.3 |
| 5,679,334 * | 10/1997 | Semoff et al. | 424/76.4 |
| 5,767,196 | 6/1998 | Kozulic | 204/466 X |
| 5,945,100 * | 8/1999 | Fick | 424/93.21 |

FOREIGN PATENT DOCUMENTS 2-054162 * 2/1990 (JP) .

* cited by examiner

*Primary Examiner*—Jeffrey Snay
*Assistant Examiner*—John S. Starsiek, Jr.
(74) *Attorney, Agent, or Firm*—Jagtiani & Associates

(57) ABSTRACT

The present invention provides electrophoresis apparatus and electrophoresis methods employing gellan gum based gels employing divalent metal cation and diamine cross-linking agents. The gels are reversible under conditions that do not damage the biomolecules separated using the gels. The present invention also provides novel gellan gum-based gels which are cross-linked which employ a diamine cross-linking agent.

24 Claims, 5 Drawing Sheets

ELECTROPHORESIS GELS

RELATED APPLICATION

The present application is based on U.S. Provisional Patent Application No. 60/073,756 filed Feb. 5, 1998 the entire disclosure and contents of which is hereby incorporated by reference.

BACKGROUND OF THE INVENTION

1. Field of the Invention

The present invention relates to electrophoresis gels and apparatuses.

2. Description of the Prior Art

In the field of electrophoresis of biomolecules such nucleic acids, peptides and proteins, various kinds of gels have been used as the electrophoresis medium. For example, U.S. Pat. No. 5,143,646 describes the use of polysaccharide gel blends for stacking electrophoresis systems, including gels which are said to be "thermoreversible" and "pH reversible", that is the gels can be liquefied by melting the polymer at high temperatures or changing the pH to neutralize the charge on the gel. It is desirable that the gels used in electrophoresis be reversible so that sections of the gel medium containing each of the different biomolecules can be liquefied and the desired molecules recovered from the liquid solution.

However, in the case of many of the gels described in U.S. Pat. No. 5,143,646, the thermoreversible gels can only be made liquid at relatively high temperatures of 65° C. or greater which that can damage many biomolecules and denature protein molecules. Similarly, the pH reversible gels described in this patent require pH of 3 or less which can also denature or damage protein molecules. Therefore, there exists a need for electrophoresis gel which is reversible at relatively mild conditions which will not damage the biomolecules to be recovered from the liquefied gel.

SUMMARY OF THE INVENTION

It is therefore an object of the present invention to provide an electrophoresis apparatus having a gel which is reversible under relatively mild conditions.

It is another object of the present invention to provide a method for recovering biomolecules using such an apparatus.

It is yet another object of the present invention to provide an electrophoresis gel which is reversible under relatively mild conditions.

According to one aspect of the present invention, there is provided an electophoresis apparatus comprising: an electrophoresis medium comprising a gel comprising gellan gum and a cross-linking agent comprising a divalent metal cation; and a means for exposing said electrophoresis medium to an electric field.

According to a second aspect of the present invention there is provided an electophoresis apparatus comprising: an electrophoresis medium comprising a gel comprising gellan gum and a cross-linking agent comprising a diamine; and a means for exposing said electrophoresis medium to an electric field.

According to a third aspect of the present invention there is provided a method for recovering a biomolecules comprising the steps of: adding a mixture containing a biological material to an electrophoresis medium comprising a gel including gellan gum and a divalent metal cation cross-linking agent; exposing said electrophoresis medium to an electric field to separate in said electrophoresis medium said biological material from other compounds in the mixture; removing a zone of the electrophoresis medium containing the biological material from the electrophoresis medium; and recovering the biological material from the removed zone of the electrophoresis medium.

According to a fourth aspect of the present invention there is provided a method for recovering a biomolecule comprising the steps of: adding a mixture containing a biological material to an electrophoresis medium comprising a gel including gellan gum and a diamine cross-linking agent; exposing said electrophoresis medium to an electric field to separate in said electrophoresis medium said biological material from other compounds in said mixture; removing a zone of the electrophoresis medium containing the biological material from the electrophoresis medium; and recovering the biological material from the removed zone of the electrophoresis medium.

According to a fifth aspect of the present invention there is provided a gel comprising gellan gum cross-linked by a diamine.

BRIEF DESCRIPTION OF THE DRAWINGS

The invention will be described in conjunction with the accompanying drawings, in which.

DETAILED DESCRIPTION OF THE PREFERRED EMBODIMENT

Definitions

Figure 1:
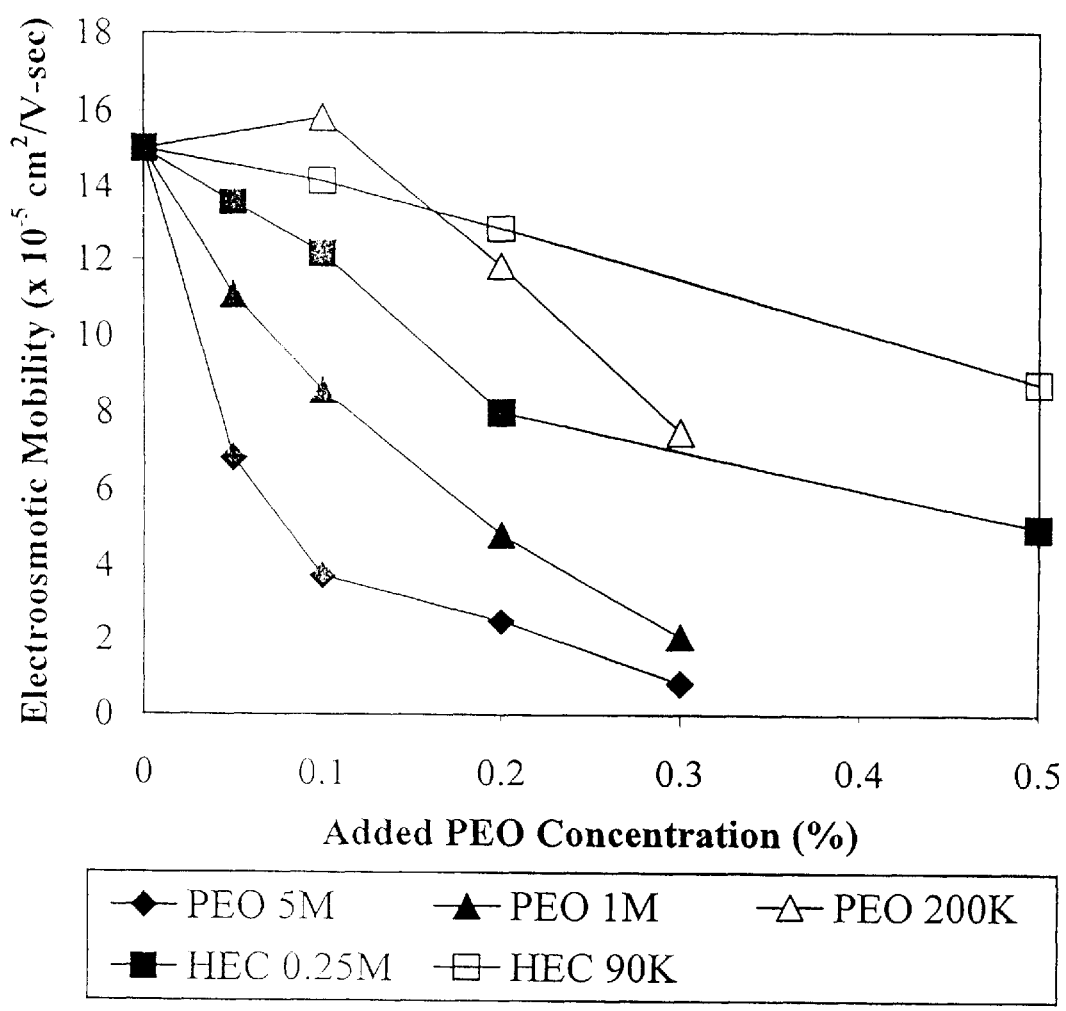
FIG. 1 is a graph illustrating the effect of polymer type and molecular weight on the electroosmotic flow in 0.2% gellan electrophoresis gels of the present invention.

For the purposes of the present invention, the term "divalent metal cation" refers to divalent group IIA cations such as $Ca^{+2}$, $Mg^{+2}$, $Sr^{+2}$, $Ba^{+2}$, etc. and to divalent transition metal cations such as $Zn^{+2}$, $Mn^{+2}$, $Cu^{+2}$, etc.

For the purposes of the present invention, the term "diamine" refers to compounds having two or more amine functional groups such as ethylene diamine, hydroxy propane diamine, etc. Although the diamines of the present invention preferably only include two amino groups, in some applications, it may be desirable to use diamines having three or more amino groups. For example, the "diamines" of the present invention include star-shaped dendrites in which there are amino groups at the end of each arm of the star. Typically, the amine groups are separated from each other by a hydrocarbon or hydrocarbon derivative chain.

For the purposes of the present invention, the term "biomolecules" includes nucleic acids, oligonucleotides such as DNA and RNA, peptides, proteins, and other biological materials commonly separated using electrophoresis techniques.

For the purposes of the present invention, the term "gellan gum" refers to a family of related carbohydrate polymers produced by Sphinogomonas bacteria (previously identified as Pseudomonas) and would include gellan gum produced by genetically engineered bacteria and chemically modified gellan gums.

For the purposes of the present invention, the term "oligonucleotides" refers to chains of one or more nucleic acids and derivatives thereof. Examples of oligonucleotides include: DNA (both single and double stranded), RNA, etc. For the purposes of the present invention, the term "polypeptides" refers to molecules including two linked amino acids and derivatives thereof.

For the purposes of the present invention, the term "size-separation property modifying polymer" refers to polymers that can be incorporated into the gel of the electrophoresis medium to alter the size-separation properties of the electrophoresis medium of the present invention. Examples of size-separation property modifying polymers include: hydroxyethyl cellulose, dextran, ficoll, polyethylene oxide, polyacrylamide, etc.

For the purposes of the present invention, the term "reversibility" is used to refer to the ability of gellan gels to be returned to a liquid state.

For the purposes of the present invention, the term "zone" refers to a portion of an electrophoresis medium or gel contains substantially one biological material. Depending on the purity desired in a particular application of the present invention, there may be some degree of other biomolecules in a given zone in addition to the biological material which is to be recovered using the method of the present invention.

Description

The present invention provides a novel apparatuses and methods for the high-resolution separation and recovery of nucleic acids, proteins and similar biomolecules. The present invention also provides novel reversible electrophoresis gels.

The gels of the present invention are based on the carbohydrate polymer, gellan gum, that has a number of unique properties. Gellan gum forms gels under certain conditions and can be returned to a liquid solution by changing the conditions (reversibility). These gels are suitable for high resolution electrophoresis and the recovery of the separated nucleic acids and proteins. In general, the separation and recovery methods of the invention consist of the following steps: (1) performing electrophoresis on a sample of one or more biomolecules in a cross-linked gellan gel electrophoresis medium (2) removing one or more separated bands or sections (zones) of gel from the electrophoresis medium and (3) changing the condition in each of the removed zone to convert the gel in the zone into a liquid solution. In a preferred embodiment a removed zone of gel containing biological material may be contacted with a membrane, followed by changing the condition of the gel so that the gel returns to solution. The biological material left behind on the membrane may then be recovered by conventional means.

The present invention provides of novel electrophoresis gels that can be made to revert to a liquid solution by changing the ionic composition or the pH of the gels. The gels have many properties that make them suitable for the purification and manipulation of biomolecules. The gels of the present invention can be formed at low concentrations of gellan gum. The conditions for causing the gels to revert to a liquid state that the delictate biomolecules contained in the gels are not damaged. The nucleic acid or protein can separated from the the liquefied gellan gum by precipitation or other methods. The electrophoretic properties of the gels of the present invention can also be modified by the addition of polymers or compounds.

Gellan gum is a linear carbohydrate polymer produced by bacterial fermentation as described in U.S. Pat. Nos. 4,326, 052; 4,377,636; 4,385,123 and European Patent No. 0 012 552, the entire disclosure and contents of which are hereby incorporated by reference. The carbohydrate polymer consists of repeats of tetrasaccharide units composed of two glucose sugars, a rhamnose and a glucuronic acid as described in O'Neil et al, "Structure of the Acidic Polysaccharide by *Pseudomonas elodato*" in Carbohydrate Research (1983), 124, 123–133 and Jansson et al, "Structural Studies of Gellan Gum, an Extracellular Polysaccharide Elaborated by *Pseudomonas elodato*" in Carbohydrate Research (1983), 124, 135–139. The gellan gum produced by fermentation has both O-acetyl and O-L-glyceryl 3-linked to glucose units. The acetyl groups can be removed during processing and the resulting materials are called low acyl gellan gums as described in Sanderson *Food Gels,* P. Harris (ed.) Elsevier Applied Science, (New York: 1990), 202–232. Commercially available low acyl gellan gums are called Gelrite and Phytagel.

Physical studies using X-ray crystallography have shown that crystals of gellan gum are intertwined, threefold left-handed parallel double helixes. Ions are believed to promote the association of the intertwined double helix molecules in solution, resulting in gel formation as described in Rinaudo, "Gelation of Ionic Polysaccharides in *Gums and Stabilizers for the Food Industry,* Phillips et al. (ed.) (Oxford: 1988), 119, Chandrasekaran et al., "The Crystal Structure of Gellan" in *Carbohydrate Research* (1988) 175, 1–15 and in Chandrasekaran et al., "Cation Interactions in Gellan: An X-ray Study of the Potassium Salt" in *Carbohydrate Research* (1988), 181, 23–40.

Gellan gum has been used in food applications as a thickening agent and in plant tissue culture as described in Sanderson *Food Gels,* P. Harris (ed.) Elsevier Applied Science, (New York: 1990), 202–232. A procedure has recently been developed that removes the residual divalent ions in commercial preparations of gellan gum, as described in Doner and Dowds, "Purification of Commercial Gellan to Monovalent Cation Salts Results in Acute Modification of Solution and Gel-Forming Properties" in *Carbohydrate Research* (1995), 273, 225–233, and replaces them with a monovalent cation such as potassium or sodium. This procedure results in a chemically defined preparation that is soluble in water.

U.S. Pat. No. 5,143,646 describes the use of polysaccharide gel blends for stacking electrophoresis systems. This patent mentions using a large number of the polysaccharide gels which form polymers, including gellan gum for its mixtures. The gels in this patent are said to be "thermoreversible", the gels can be liquefied by melting the polymer at high temperatures, and "pH reversible", the gels can be liquefied by changing the pH to neutralize the charge on the gel. Because gellan has carboxy groups, liquefying gellan using the method described in this patent would require reducing the pH of the gel to less than 3 to protonate the carboxyl groups. However, at pH levels this low, any proteins or nucleic acids in the gellan could be denatured or broken down. With respect to temperature reversibility, for a typical gel described in U.S. Pat. No. 5,143,646, such as low melting point agaroses, the temperature must be raised to 65° C. to liquefy the gel. Just like excessively low pH, such high temperatures can degrade the biomolecules contained in a gel.

In contrast to the gels described in U.S. Pat. No. 5,143, 646, the gels in of the present invention do not require high temperatures of pH extremes. In one embodiment, the pH reversible gels cross-linked with a diamine can be liquefied (reversed) by the deprotonation of the diamine. Because the diamines used in the present invention preferably have pKs close to neutrality (pH 7), the gels containing them are reversible by changing the pH at around 7. At pH below 7 a gel will form and above pH 7 the gel will reverse to a liquid solution. The pH reversibility of the gels of present invention, in contrast to previous reversible electrophoresis gels, is based changing the state of a cross-linker for the gel and not the gel. For applications of the present invention where it is desirable to operate at pHs other than neutrality, the pH at which the gel liquefies can be adjusted by changing the chemical nature of the diamine used to form the gel.

The electrophoresis gels of the present invention can be formed using gellan gum in a wide range of concentrations, preferably from 0.03 to 2 grams per 100 mL. The gellan gum is dissolved in water or a buffer solution by mixing the gel into the solution. The solution can be heated to decrease the time necessary to dissolve the polymer particles.

The gellan gum can be cross-linked using either a divalent metal cation or a diamine. Where the cross-linking agent is a divalent metal cation, a variety of divalent metal cations can be used such as group IIA metal cations, such as $Ca^{+2}$, $Mg^{+2}$, $Sr^{+2}$, $Ba^{+2}$, etc., or transition metal cations such as $Zn^{+2}$, $Mn^{+2}$, $Cu^{+2}$, etc. The divalent metal cations are generally added to the gellan gum solution in the form of a metal salt. Typically the gellan gum polymer is mixed with the divalent metal cation cross-linking agent at a temperature above 60° C. and the solution is allowed to cool to form the gel. The divalent metal cation is preferably added to the electrophoresis buffer solution used in conjunction with the electrophoresis medium, preferably at a concentration of 0.1 to 10 mmol/L. Circulation of the buffer helps to prevent depletion of the divalent metal cation in the gel. Electrophoresis can be done in a variety of conventional formats including flat bed apparatus, vertical slab apparatus, tubes, and capillary tubes.

In the case of divalent metal cation cross-linked gels, after electrophoresis, the separated bands can be detected using a variety of means including specific stains or direct scanning of the gel. The bands containing the isolated solutes (biomolecules) can be recovered by a variety of means including adding a chelating compound specific for the divalent cation used to for the gel in solution form or attached to a solid substrate, such as an ion exchange resin.

Electrophoresis gels of the present invention employing diamine cross-linking agents can be formed in a similar manner to the gels using divalent metal cation cross-linking agent by mixing the diamine with the gellan gum polymer at a temperature above 60° C. Any buffer used in conjunction with the diamine cross-linked gels of the present invention should maintain the gel at a pH below the pK's of the amino groups of the diamine so that the amino groups are protonated.

In the case of diamine cross-linked gels, after electrophoresis, the separated bands can be detected using a variety of means including specific stains or direct scanning of the gel. The bands containing the isolated solutes (biomolecules) can be recovered by a variety of means including adding a base to the gel either in solution form or attached to a solid substrate, such as an ion exchange resin. Once the pH of the gel is increased to the point where the amino groups of the diamine cross-linking agent are not longer full protonated, the gel reverts to a liquid solution.

In the case of either divalent metal cation cross-linked gels or diamine cross-linked gels fo the invention, the properties of the electrophoresis gels of the present invention can be modified by the incorporation of additional polymers in the gel. For example, polymers can be incorporated in a gel to reduced the osmotic flow, and, thereby, increase the resolution of oligonucleotides and proteins by the gel.

The present invention will now be described by way of the following examples:

EXAMPLE 1

Properties of Gellan Gum Electrophoresis Gels and Modifications of Electroosmotic Flow by Additional Polymers Gel Formation, Electrophoresis, and Measurement of Electroosmotic Flow Gellan gum (potassium salt ) was prepared using a deionization and precipitation procedure described in Doner et al., "Purification of Commercial Gellan to Monovalent Cation Salts Results in Acute Modification of Solution and Gel-Forming Properties" in *Carbohydrate Research* (1995), 273, 225–233. The gellan gum powder was placed in a flask along with water and heated to boiling with stirring. The solution was stirred for 10 min to ensure that all particles of the polymer were dissolved. At this point additional polymers were added. Either the dry power or a concentrated liquid solution of the additional polymer was added and the solution stirred for an additional 10 min. In some cases the solution was heated to facilitate the dissolution of the added polymer. A concentrated solution (50 mmol/L) of either $CaCl_2$, or 1,3 diamino-2-hydroxypropane (DAHP) was added so that the final concentration was 5 mmol/L. A solution of buffer (10-fold concentrated) was also added. The solution was stirred for an additional 10 min. The temperature of the solution was reduced to approximately 60° C. and the solution poured into the gel tray and allowed to solidify. A comb (16 teeth, 2 mm thick) was then suspended in the gel to form the sample wells. A flat bed submarine gel electrophoresis apparatus was used. The electrode buffer chambers were circulated by means of a peristaltic pump. The samples were diluted with a solution so the samples contained Ficoll 400,000 molecular weight (2% final concentration) or sucrose (5% final concentration), a trace of bromophenol blue, and the electrophoresis buffer. The samples were loaded into wells and the electric field applied. Measurement of electroosmotic flow in the gels was determined by measurement of the mobility of cyancobalamin.

The buffers used for the gellan gum electrophoresis are shown in Table 1 below:

TABLE 1

Buffers Used for Gellan Gum Gel Electrophoresis

| Buffer | Composition | pH |
| --- | --- | --- |
| TB | 0.045 mol/L tris(hydroxymethyl)aminomethane (Tris) and 0.045 mol/L boric acid | 8.5 |
| TA | 0.04 mol/L TRIS and 0.1 mol/L acetic acid | 8.3 |

TABLE 1-continued

Buffers Used for Gellan Gum Gel Electrophoresis

| Buffer | Composition | pH |
|---|---|---|
| TG | 0.0039 mol/L TRIS and 0.047 mol/L glycine | 8.3 |
| BBE | 0.022 mol/L bis (2-hydroxethyl) imino-tris (hydroxymethyl) methane, 0.045 mol/L boric acid, and 0.001 mol/L EDTA | 6.8 |

Table 2 below shows the absorbance values for gellan gum gels in the ultraviolet range. The gels were dissolved in water (blank) formed using 5 mmol/L $CaCl_2$.

TABLE 2

Absorbance Values of Gellan Gum Electrophoresis Gels

| Gel Concentration | 240 nm | 260 nm | 280 nm | 300 nm |
|---|---|---|---|---|
| 0.05% | 0.164 | 0.122 | 0.090 | 0.064 |
| 0.1% | 0.234 | 0.176 | 0.130 | 0.088 |
| 0.2% | 0.465 | 0.349 | 0.256 | 0.172 |

The low absorbance of the gels in Table 2 makes it possible to detect nucleic acids and proteins directly in the gel without staining. FIG. 1 shows the effect of incorporating additional polymers into the gellan gum electrophoresis gels. FIG. 1 is a graph illustrating the effect of polymer type and molecular weight on the electroosmotic flow in 0.2% gellan gum gels. The gels were cast with 5 mmol/L $CaCl_2$ and the buffer (0.0039 mol/L TRIS and 0.047 mol/L gylcine). Electrophoresis was at 2 V/cm for 4 h at 20° C. Electroosmotic flow was determined by measuring the mobility of cyanocobalamin. The polymers used were polyethylene oxide (PEO) or hydroxyethyl cellulose (HEC). The molecular weights were 5,000,000 (5M), 1,000,000 (1M), 250,000 (0.25M), 200,000 (0.2M), and 90,000 (90K).

Figure 2:
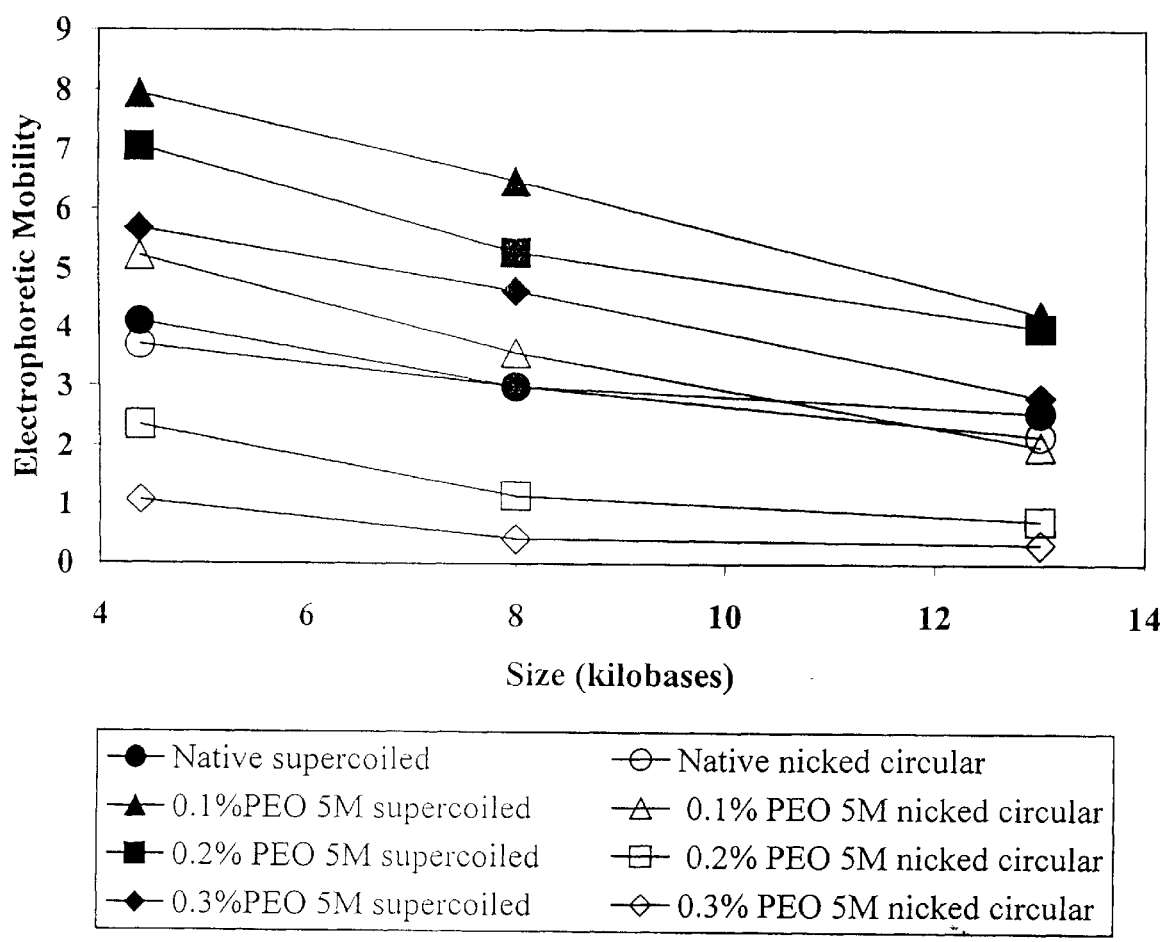
FIG. 2 is a graph showing the effect of polyethylene oxide 5,000,000 (PEO 5M) on the separation of supercoiled plasmid (SC) or nicked circular plasmid (NC) in a gellan electrophoresis gel of the present invention.

As seen in FIG. 1, increasing the concentration of additional polymer greatly reduces the electroosmotic flow in the gels. FIG. 1 shows that higher molecular weight polymers, such as polyethylene oxide (PEO), are more effective at reducing electroosmotic flow compared to lower molecular weight polymers. A variety of polymers both linear and branched can be incorporated into the gellan gum electrophoresis gels to modify their properties. Some examples of polymers which can be used include: dextran, Ficoll, amylose. alginates, amylopection, xanthan gum, Whelan gum, hydroxethyl cellulose, methyl cellulose, polyvinylpyrrolidone, and polyvinylalchol. FIG. 2 shows the effect of the increasing amount of PEO (5,000,000 molecular weight) on the separation of supercoiled (SC) and nicked circular (NC) plasmid DNA. The plasmids used were pBR 322 (4.3 kilobases), pDelta (8.0 kilobases), and pYA101 (13 kilobases). Electrophoresis was at 5 V/cm at 20° C. for 4 h. The buffer used was BBE (0.022 mol/L bis (2-hydroxethyl) imino-tris (hydroxymethyl) methane, 0.045 mol/L boric acid, and 0.001 mol/L EDTA). These results show that the mobility of the nicked circular form can be reduced to near zero while the supercoiled form has significant mobility. This allows for a very efficient separation between the two different physical forms of DNA.

EXAMPLE 2

DNA Electrophoresis Using Gellan Gum Formed Using Divalent Cations and a Diamine Gel Formation and Electrophoresis Gel formation was as described in Example 1. The gels were stained with ethidium bromide (1 μg/mL) with gentle mixing for 0.5 to 1 h in a solution of 0.1 mol/L KCI. The gels were destained for 0.5 h in a solution of 0.1 mol/L KCL.

Results

Figure 3:
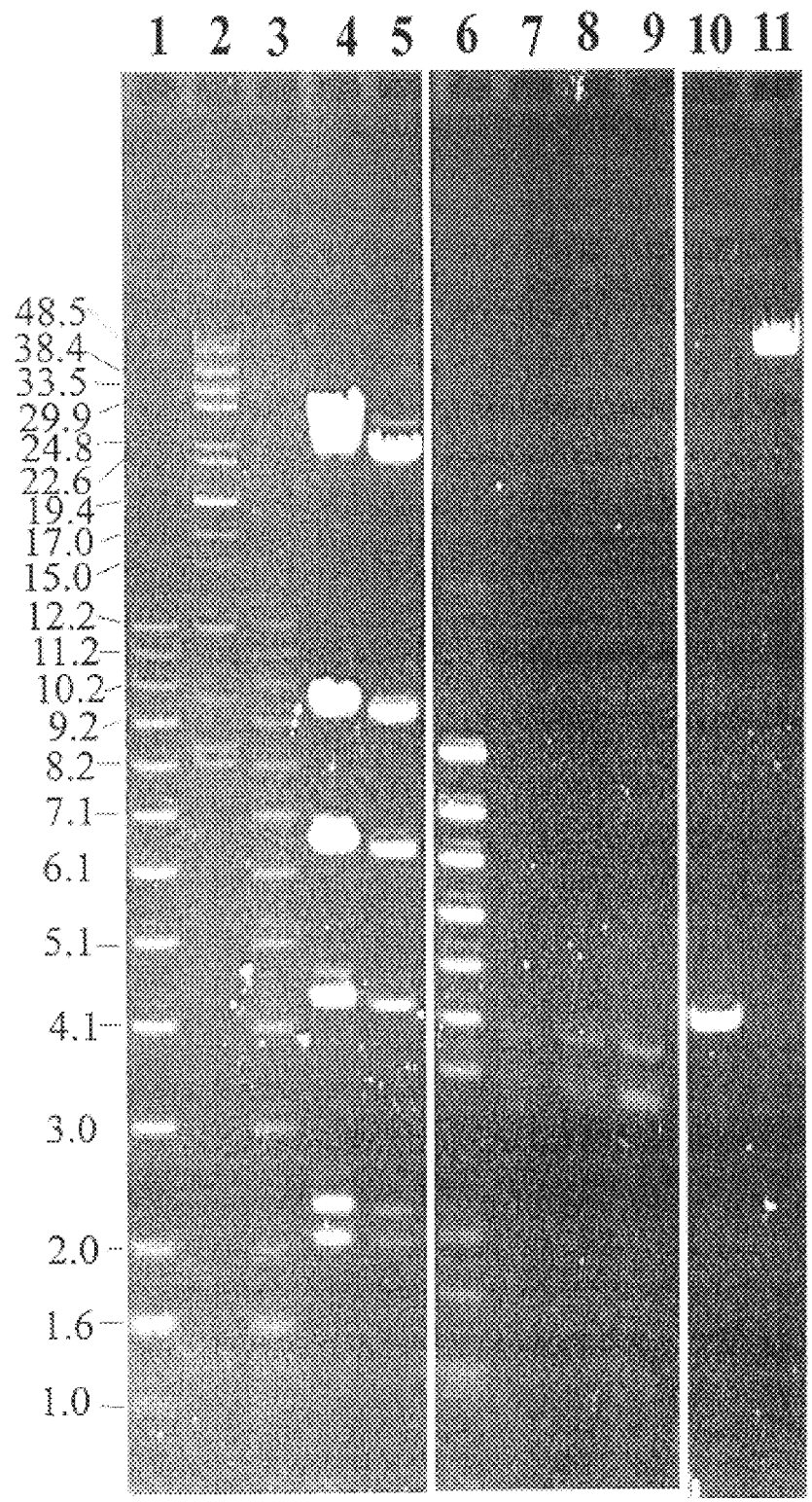
FIG. 3 is a picture of a gel electrophoresis of DNA using a gellan electrophoresis gel of the present invention cross-linked by $Ca^{+2}$.

FIG. 3 shows the results of an electrophoresis gel made from gellan with the use of calcium cations. FIG. 3 is an image of a DNA electrophoresis gel using 0.1% gellan gum gel formed with 5 mol/L $CaCl_2$. The buffer was TB, (Table 1) with 1 mmol/L $CaCl_2$ and electrophoresis was at 140 V (4.7 V/cm) for 16 h at 20° C. In FIG. 3 the samples are: Lanes 1 and 3 a Kb Ladder; Lane 2, a High Molecular Weight Ladder; Lanes 4 and 5, a Hind III restriction digest of λ DNA; Lane 6 is a BstE II restriction digest of λ DNA; Lanes 7, 8 and 9 are pBR 322 DNA (containing nicked circular and supercoiled forms); Lane 10 is a pBR 322 restriction digestion by Hind III; and Lane 11 is λ DNA (48.5 kilobase pairs). Numbers on the side of the picture indicate the size of DNA standards (lanes 1 and 2) in kilobase pairs. This gel gave good resolution of DNA from about 50,000 base pairs to about 1,000 base pairs. The resolution of DNA below 1,000 base pairs requires the addition of polymers to the gels.

Gels formed with diamines gave similar results to those made with divalent cations. The formation of gels was dependent upon the protonation of both amines. A typical diamine such as ethylenediamine has values of 10.1 and 7.0 for the amino pK's. At a pH above 7, a significant fraction of the amine groups would not be protonated and gels would not form. DNA can be recovered from gellan gum gels made with diamines by raising the pH above 7. Gel slices returned to a solution when a buffer containing 10 mmo/L TRIS pH 8.0 was added.

A variety of diamines can be used to form gels. The basic amino acids, lysine, arginine, and histidine contain two positively charged amino groups, but did not form gels when added at concentrations of 5 mmol/L at pH below 7. The methyl esters (blocked carboxyl groups) of lysine, argiine, and histidine, all formed stable gels when added at concentrations of 5 mmol/L at pH below 7. The basic amino acids with unblocked carboxyl groups do not form gels apparently due to the proximity of the carboxyl group to the α amino group. EDTA can be added to gellan gum gels and buffers when gels have been formed with diamines. EDTA is commonly added to buffers used with DNA, because the removal of divalent metal cations by chelation prevents the activity of contaminating nucleases, if present. If contaminating nucleases are likely to be a problem, gels should be formed with diamines, and EDTA included in the buffer.

Figure 4:
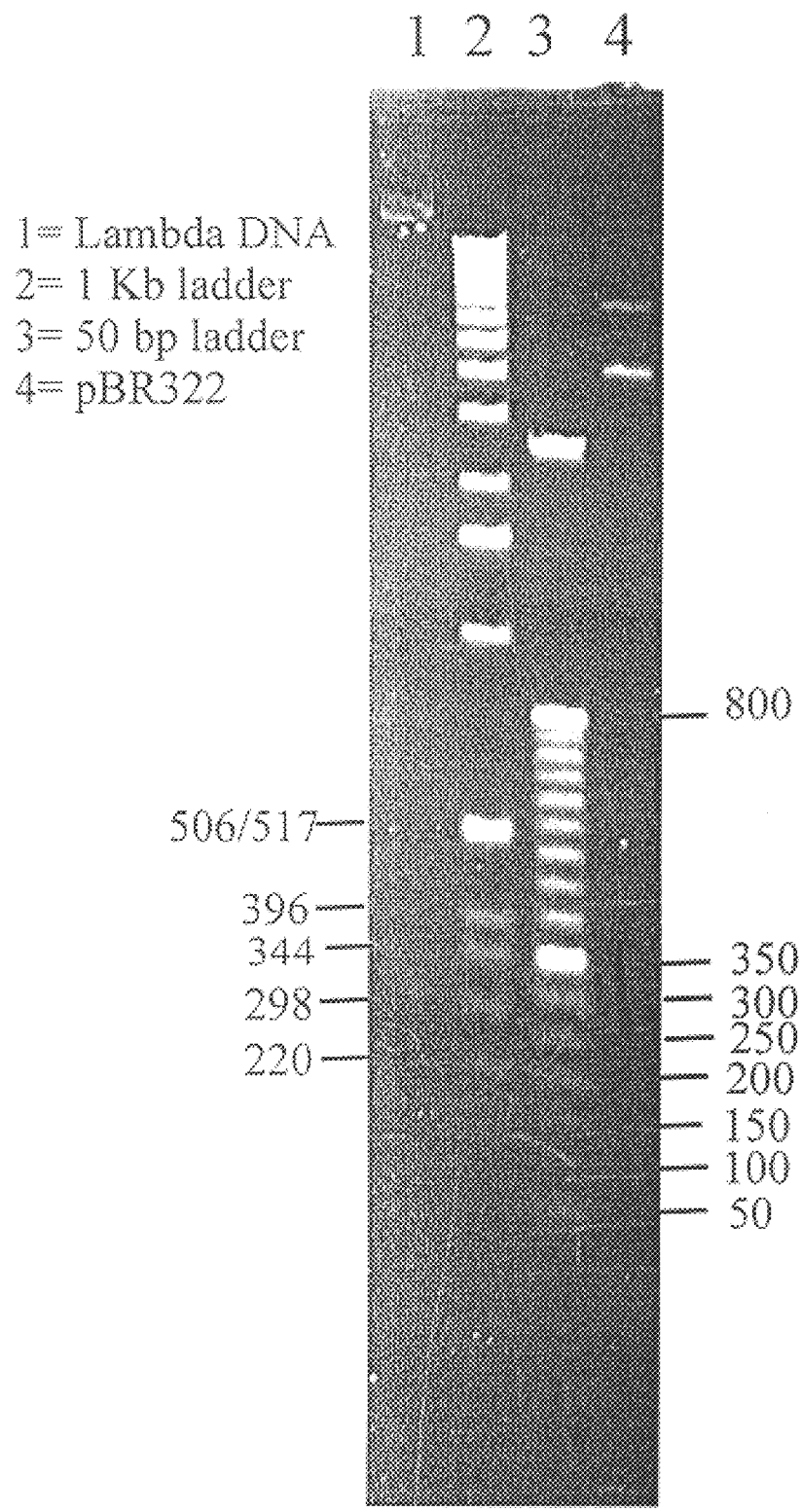
FIG. 4 is a picture of a gel electrophoresis of DNA using a gellan electrophoresis gel of the present invention cross-linked by a diamine.

The addition of addition polymers to gellan gum electrophoresis gels had two effects on the separation of DNA. The polymers increased the resolution of lower molecular mass DNA and the electroosmosis was reduced. The decreased eletroosomotic flow allowed the electrophoresis to be done in a few hours. FIG. 4 shows the separation of DNA in a gellan gum electrophoresis gel containing 1.0% hydroxethyl cellulose (250,000 molecular weight) The gel in FIG. 4 was formed using DAHP (5 mmol/L) and contained HEC (1%). The running buffer was BBED containing 1 mmol/L DAHP, and 1.0% HEC. Electrophoresis was for 2.5 h at 300 V. Lane 1 is a λ DNA sample. Lane 2 is a Kb DNA ladder sample. Lane 3 is a 50 basepair Ladder DNA sample. Lane 4 is a pBR 322 plasmid DNA sample (containing both supercoiled and nicked circular forms). This gel resolved DNA down to approximately 50 base pairs.

EXAMPLE 3

Demonstration of DNA Recovery, Enzymatic Treatment, and Transformation Using DNA Isolated From Gellan Gum Electrophoresis Gels Restriction Digestion and Ligation Bands containing DNA were excised with a blunt spatula, placed in a microfuge tube, and weighed. In the case of DNA isolated from gels cast with calcium, a concentrated solution (10-fold) of EDTA (pH 8.0) was added to the gel slice so the final concentration was 2 mmol/L. In the case of DNA isolated from gels cast with DAHP, a concentrated solution (10-fold, pH 7.5) of TRIS and EDTA was added to the gel slice so the final concentrations were 10 mmol/L and 1 mmol/L, respectively. Gentle mixing was sufficient to dissolve the gel. The restriction enzyme (10 units) or ligase (1 unit) was added directly to the dissolved gel band and the solution was mixed. The 10× restriction or 5× ligase buffer (Life Technologies, Rockville, Md.) was added, the tubes mixed, and incubated at 37° C. for 2 h to 4 h.

Transformation Efficiency

The effect of the gel on transformation efficiency was determined using chemically competent $E.$ $coli$ cells. DNA from gellan gum electrophoresis gels was isolated as described above. The dissolved gel solution (0.05 mL) was placed on ice and competent cells (0.05 mL) were added to tubes containing the dissolved gel or buffer (final volume of 0.1 mL). Transformation was done according to the supplier's instructions. Briefly, this consisted of incubation on ice for 30 min, heat shock at 37° C. for 45 sec., back on ice for 2 min, and addition of 0.95 ml of LB media. The tubes were then incubated at 37° C. with shaking (225 rpm) for 1 h. The cells were diluted and plated out on LB plates containing 0.1 mg/mL ampicillin. Colonies were counted the next day after incubation at 37° C.

Results

DNA isolated from gellan electrophoresis gel was readily cut by a variety of restriction enzymes (Eco RI, Hind III, and Bst EII) in the presence of gellan gum. This was determined by analysis of the restriction fragment using agarose gel electrophoresis. The activity of DNA ligase was not significantly inhibited by gellan gum as shown by the ligation of a test mixture of restriction fragments. Successful ligation of the test mixture was indicated by the formation of higher molecular weight products when analyzed by agarose gel electrophoresis. DNA isolated from gellan gum electrophoresis gels was readily ligated as shown by the formation of higher molecular weight products when analyzed on agarose gel electrophoresis.

DNA isolated from gellan gum electrophoresis gels after dilution could be used in direct transformation of $E.$ $coli$ as shown in Table 3 below. DNA isolated from gellan gum electrophoresis gels and ligated to other DNA did not transform with high efficiency unless the gellan gum was removed before or after ligation. This is because of the high concentration of $Mg^{+2}$ in the liation buffer causes the formation of a gel that inhibits transformation. Adding $CaCl_2$, to the ligation mixture followed by centrifugation precipitates the gellan into a compact pellet and leaves the DNA in solution. The DNA will transform with high efficiency.

These experiments show that enzymatic manipulation of the DNA can be done in the presence of the gel polymer. Restriction enzyme digestion and ligation of DNA are several of the most commonly used steps used in molecular biology laboratories. An important step in cloning is to use exogenous DNA to transform bacteria. The data Table 3 below shows that gellan gum polymer does not inhibit the transformation of $E.$ $coli$ cells by pBR 322 plasmid DNA. The gellan gum polymer was added to a preparation of pBR 322 plasmid DNA and then the mixture was used to transform $E.$ $coli$ cells. An aliquot (0.1 mL of a 1:10 dilution) of the transformation reaction was plated on LB plates containing ampicillin and the colonies counted.

The results of this experiment are summarized below in Table 3:

TABLE 3

Effect of Gellan Gum on Transformation of $E.$ $coli$ by pBR Plasmid DNA

| Gel % (before adding cells) | Ampicillin Resistant Colonies per microgram of plasmid DNA (average of two plates) |
|---|---|
| 0 | $1.9 \times 10^6$ |
| 0.02 | $2.4 \times 10^6$ |
| 0.05 | $1.7 \times 10^6$ |
| 0.02 (HEC 250K 0.2%) | $1.6 \times 10^6$ |
| 0.05 (HEC 250K 0.5%) | $2.4 \times 10^6$ |

These results show that the presence of gellan gum in the DNA sample did not inhibit transformation of $E.$ $coli$. The presence of the polymer hydroxethyl cellulose 250,000 molecular weight (HEC 250K) along with gellan did not significantly inhibit transformation. Many of the critical steps in the manipulation and cloning of DNA, including restriction digestion, ligation, and transformation of bacteria by DNA isolated from these gels can be done in the presence of the gellan gum polymer.

EXAMPLE 4

Electrophoresis of Proteins Using Gellan Gum Gels

Gel Formation, Electrophoresis, and Staining of Proteins

Gels were formed as described in Example 1. After electrophoresis the gels were fixed in either 50% ethanol, 2% phosphoric acid or 10 mmol/L HCl for 1 h. The gels were washed in 1 mmol/L HCl and then stained in Coomassie Brilliant Blue G250 (0.015 mg/mL) in 1 mmol/L HCl overnight. The gels were destained in 1 mmol/L HCl for a few hours.

Several standard proteins and crude protein mixtures, such as milk, were used to determine the separation of proteins using gellan gum gels.

These proteins have different isoelectric points and electrophoretic mobilities, shown in Table 4 below.

TABLE 4

Properties of Proteins

| Protein | Abr. | Molecular Mass | Isoelectric Point | Electrophoretic Mobility in TG buffer $(cm^2/V \cdot s) \times 10^{-5}$ |
|---|---|---|---|---|
| Myoglobin (horse heart) | MYO | 17,500 | 7.4 | 5.8 |
| β Lacto-globulin (mixture of A and B) | BLG | 36,700 (dimer) | 5.2 and 5.3 | 27.2 and 25.3 |
| α Lactalbumin | ALA | 14,400 | 4.8 | 19.4 |

TABLE 4-continued

Properties of Proteins

| Protein | Abr. | Molecular Mass | Isoelectric Point | Electrophoretic Mobility in TG buffer (cm$^2$/V · s) × 10$^{-5}$ |
|---|---|---|---|---|
| Bovine Serum Albumin | BSA | 68,000 | 4.9, 4.7 | 28.9 |
| Cyctochrome c | CYT | 12,500 | 10.2 | — |

Results

Figure 5:
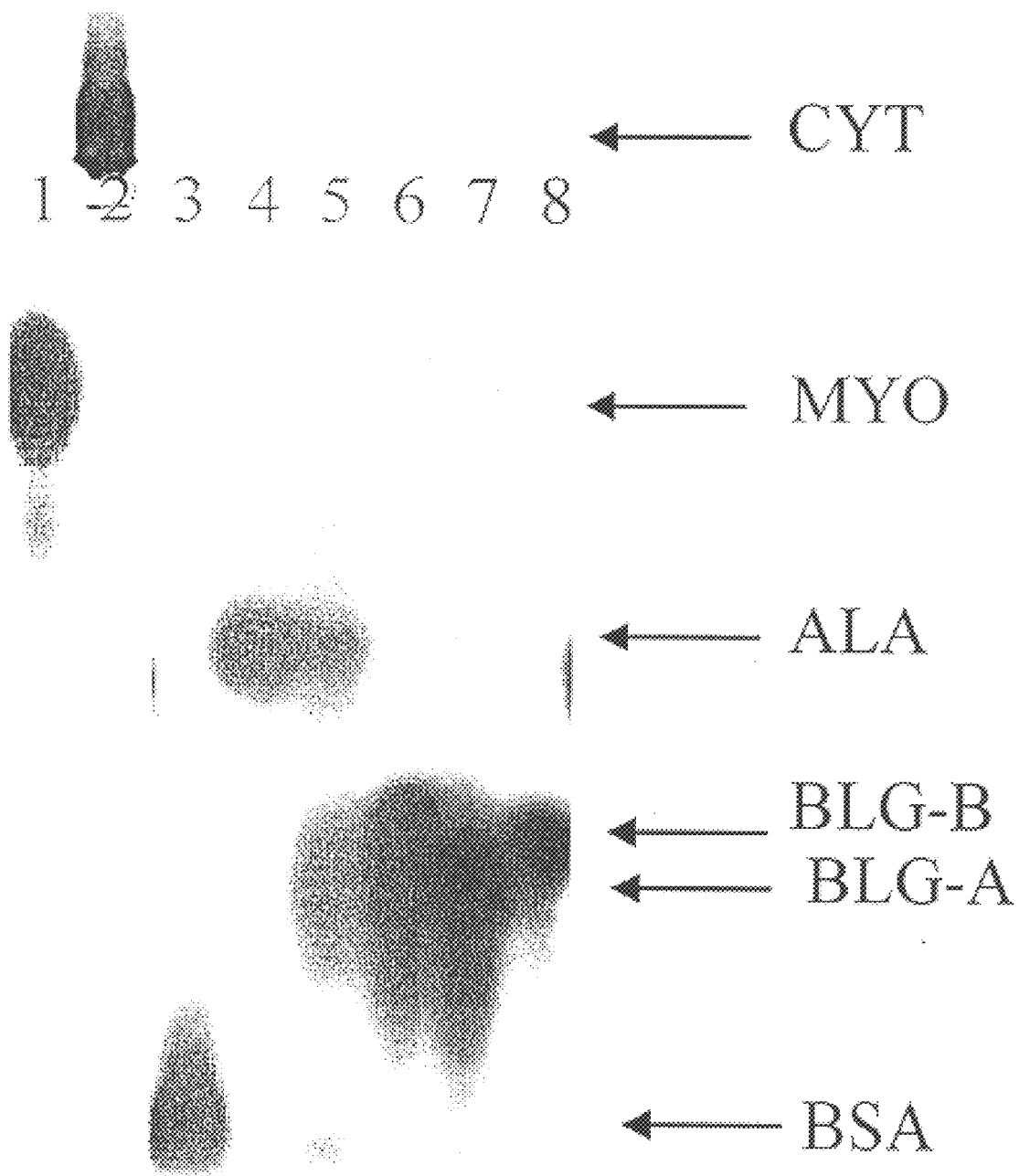
FIG. 5 is a picture of a gel electrophoresis of proteins in a gellan electrophoresis gel of the present invention which contains polyethylene oxide.

The net charge and electrophoretic velocity of proteins was be determined by the pH of the buffer used. When the buffer TG with a pH of 8.3 was used all of the above proteins were negatively charged with the exception of cytochrome c. These proteins would be expected to migrate towards the positive electrode. On a gellan gum electrophoresis gel the considerable electroosmotic flow carries the proteins toward the negative electrode. Negatively charged proteins with the lowest electrophoretic mobility will migrate toward the negative electrode. Negatively charged proteins with higher electrophoretic mobility (oppose electroosmotic flow to a greater extent) migrate towards the negative electrode at a lower rate, Since gellan gum is negatively charged, positively charged proteins can adsorb to the gel and are slowed in their migration toward the negative electrode. Adding additional polymers to the gel can reduce the electroosmotic flow so that negatively charged proteins will migrate towards the positive electrode. FIG. 5 shows the electrophoresis of proteins in an 0.2% gellan gum electrophoresis gel containing 0.2% polyethylene oxide 5,000,000. The buffer used was TG. Electrophoresis was conducted at 2 V/cm for 20 min and 8.6 V/cm for 184 min at 20° C. The samples were: lane 1, myoglobin; lane 2, cytochrome c; lane 3, bovine serum albumin; lane 4, α-lactalbumin; lane 5, bovine whey mixture; lane 6, β-lactoglobulin; lane 7, β-lactoglobulin A; lane 8, β-lactoglobulin B. As seen in FIG. 5, the protein with the highest electrophoretic mobility (bovine serum albumin) moved the greatest distance towards the positive electrode. This gel shows the partial resolution of β-lactoglobulin A and B which differ, in electrophoretic mobility by about 8.5%. FIG. 5 also shows that cytochrome c is adsorbed to the gel and does not migrate significantly towards the negative electrode.

These results with proteins indicate that a number of variables can be modified to achieve selective separations. The pH appears to directly determine the charge on the protein and the electrophoretic mobility. Proteins with greater positive charge will adsorb to the negatively charged gel and will be slowed in their migration. The ionic strength of the solution influences adsorption to the gel polymer. The amount of electroosmotic flow in the gel can be controlled and a protein's net migration determined by the magnitude of the electroosmotic flow and the electrophoretic mobility. Additional interactions between the proteins and additional polymers will also determine the separation.

EXAMPLE 5

Formation of Gellan Electrophoresis Gels Based on Disulfide Bonds

Proteins are examples of polymers that can be cross-linked through reversible disulfide bonds. Cysteine is an amino acid containing a free sulhydryl (thiol) side chain. Cysteine can be readily oxidized to for cystine, which contains two cysteines linked at the side chains through a disulfide bond. This is the method nature has evolved to reversibly cross-link proteins. The methyl esters of cystein and cystine have blocked carboxyl groups and free amino groups. Strong stable gels were formed when cystine dimethyl ester (0.005 mol/L) in 0.01 mol/L TRIS buffer pH 7.0 was used to form a gellan electrophoresis gel (0.1%). Cysteine methyl ester (0.01 mol/L) did not form gels under the same conditions. A solution of dithiothreitol (0.05 mol/L, final concentration) when added to a gellan electrophoresis gel (0.01%) formed with cystine dimethyl ester converted the gel back to solution. These experiments show that gellan electrophoresis gels can be made using disulfide bonds and returned to solution using reducing solutions.

Although the above-described gellan electrophoresis gel uses a diamine (cystine dimethyl ester) to form a gel, thiol groups can also be introduced into the gellan gum polymer by covalent bonds. Gellan gum has a charged carboxyl group that binds cations. The carboxyl groups can also be used as an attachment point to make various gellan gum derivatives. The carboxyl group is a reactive site to which can be covalently attached thiol or other functional groups. The carboxyl group reacts with other groups such as amines when used with compounds such as carbodimides. Carbodimides will promote the condensation of an amine and a carboxyl group. A derivative of gellan gum containing free sulfide groups covalently attached to the carbohydraate chain can be made by such organic chemistry. For instance, if gellan gum is reacted with a compound such as 2-mercaptoethylamine and a carbodiimide. The carboxyl group and amine form an amide. Other reactions can be sued to introduce covalently bound sulfhydryl groups to form disulfides. Such a gel has the advantage of having no charge and free sulfhydryl groups to form reversible gels based on the redox of the solution.

EXAMPLE 6

Method to Remove Gellan From Isolated Samples

A solution of CaCl$_2$ is added to a sample containing a target molecule, such as DNA or a protein, removed from a gellan gum electrophoresis medium cross-linked with CaCl$_2$ to a concentration of 5 mmol/L or greater. The solution is mixed and the cross-linked gellan gum is removed by centrifugation, for example at 12,000×g for 15 min, or by filtration. The gellan gum is collapsed into a compact pellet (centrifugation) or retained on a filter (filtration) leaving the target molecule in solution. This method improves the transformation efficiency by DNA in chemically competent cells Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An electrophoresis apparatus comprising a gel comprising gellan gum, a cross-linking agent comprising a divalent metal cation, and a size-separation modifying polymer; and means for exposing said electrophoresis medium to an electric field.

2. The apparatus of claim 1, wherein said at least one cross-linking agent comprises a group IIA cation.

3. The apparatus of claim 1, wherein said group IIA cation comprises $Ca^{+2}$.

4. The apparatus of claim 1, wherein said gel further includes a buffer compound for maintaining said gel at a pH of 5 to 9.

5. An electrophoresis apparatus comprising:
- an electrophoresis medium comprising a gel comprising gellan gum and at least one cross-linking agent comprising ethylene diamine; and
- a means for exposing said electrophoresis medium to an electric field.

6. The apparatus of claim 5, wherein said gel further includes a buffer compound for maintaining said gel at a pH of 5 to 9.

7. The apparatus of claim 5, wherein said gel further comprises a size-separation modifying polymer.

8. A electrophoresis apparatus comprising:
- an electrophoresis medium comprising a gel comprising gellan gum and at least one cross-linking agent comprising hydroxy propane diamine; and
- means for exposing said electrophoresis medium to an electric field.

9. The apparatus of claim 8, wherein said gel further includes a buffer compound for maintianing said gel at a pH of 5 to 9.

10. The apparatus of claim 8, wherein said gel further comprises a size-separation modifying polymer.

11. A method for recovering a biological material comprising:
- adding a mixture containing a biological material to an electrophoresis medium comprising a gel including gellan gum and a divalent metal cation cross-linking agent;
- exposing said electrophoresis medium to an electric field to separate in said electrophoresis medium said biological material from other compounds in said mixture;
- removing a zone of the electrophoresis medium containing the biological material from the electrophoresis medium;
- exposing the removed zone of electrophoresis medium to a chelating agent to chelate the divalent metal cation and, thereby, liquefy the gel of the removed zone of electrophoresis medium; and
- separating the biological material from the liquefied gel of the removed zone of electrophoresis medium, thereby recovering the biological material.

12. The method of claim 11, wherein said separation step includes centrifuging the liquefied gel containing the biological material.

13. The method of claim 11, wherein said method further comprises contacting the removed zone of the electrophoresis medium to a membrane to bind the biological material in the removed zone to said membrane prior to exposing the removed zone to said chelating agent; and wherein the biological material remains bound on said membrane after said gel is liquefied.

14. The method of claim 11, wherein said at least one cross-linking agent comprises a group IIA cation.

15. The method of claim 11, wherein said group IIA cation comprises $Ca^{+2}$.

16. The method of claim 11, wherein said gel further includes a buffer compound for maintaining said gel at a pH of 5 to 9.

17. The method of claim 11, wherein said gel further comprises a size-separation modifying polymer.

18. A method for recovering a biological material comprising:
- adding a mixture containing a biological material to an electrophoresis medium comprising a gel including gellan gum and a diamine cross-linking agent;
- exposing said electrophoresis medium to an electric field to separate in said electrophoresis medium said biological material from other compounds in said mixture;
- removing a zone of the electrophoresis medium containing the biological material from the electrophoresis medium;
- adding a pH modifying agent to the removed zone of electrophoresis medium to increase the pH and liquefy the gel of the removed zone of electrophoresis medium; and
- separating the biological material from the liquefied gel of the removed zone of electrophoresis medium, thereby recovering the biological material.

19. The method of claim 18, wherein said separation step includes centrifuging the liquefied gel containing the biological material.

20. The method of claim 18, wherein said method further comprises contacting the removed zone of electrophoresis medium to a membrane to bind the biological material in the removed zone to the membrane prior to exposing the removed zone to said pH modifying agent; and wherein the biological material remains bound on said membrane after said gel is liquefied.

21. The method of claim 18, wherein the diamine comprises ethylene diamine.

22. The method of claim 18, where the diamine comprises hydroxy propane diamine.

23. The method of claim 18, wherein said gel further includes a buffer compound for maintaining said gel at a pH of 5 to 9.

24. The method of claim 18, wherein said gel further comprises a size-separation modifying polymer.

* * * * *